(12) United States Patent
Csutak

(10) Patent No.: US 10,598,814 B2
(45) Date of Patent: Mar. 24, 2020

(54) MEASURING SOURCE ROCK POTENTIAL USING TERAHERTZ ANALYSIS

(71) Applicant: Saudi Arabian Oil Company, Dhahran (SA)

(72) Inventor: Sebastian Csutak, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/852,387

(22) Filed: Dec. 22, 2017

(65) Prior Publication Data
US 2019/0196054 A1 Jun. 27, 2019

(51) Int. Cl.
G01V 5/08 (2006.01)
G01V 8/00 (2006.01)
G01V 8/02 (2006.01)
E21B 49/02 (2006.01)
E21B 47/00 (2012.01)
G01N 21/3581 (2014.01)

(52) U.S. Cl.
CPC .......... G01V 8/005 (2013.01); E21B 47/0002 (2013.01); E21B 49/02 (2013.01); G01N 21/3581 (2013.01); G01V 8/02 (2013.01)

(58) Field of Classification Search
CPC ........ E21B 47/102; E21B 49/08; E21B 49/10; G01V 8/02; G01N 21/359
See application file for complete search history.

(56) References Cited

U.S. PATENT DOCUMENTS

| 6,815,683 | B2 | 11/2004 | Federici et al. | |
| 6,917,303 | B2* | 7/2005 | Stuart-Bruges | E21B 47/01 |
| | | | | 175/50 |
| 7,781,737 | B2 | 8/2010 | Zhdaneev | |
| 8,704,160 | B1* | 4/2014 | Zhdaneev | E21B 49/06 |
| | | | | 250/269.1 |
| 9,234,797 | B1* | 1/2016 | Newman | G01J 3/28 |
| 10,222,468 | B2* | 3/2019 | Assefzadeh | G01S 13/89 |
| 2005/0067629 | A1* | 3/2005 | Woodall | C30B 23/02 |
| | | | | 257/101 |
| 2008/0149819 | A1* | 6/2008 | Zhdaneev | G01N 21/3581 |
| | | | | 250/255 |

(Continued)

FOREIGN PATENT DOCUMENTS

EP 2021768 9/2016

OTHER PUBLICATIONS

Angrisani et al. "THZ Measuring Systems", INTECH, 2016, p. 21-48. (Year: 2016).*

(Continued)

*Primary Examiner* — David P Porta
*Assistant Examiner* — Mamadou Faye
(74) *Attorney, Agent, or Firm* — Fish & Richardson P.C.

(57) ABSTRACT

The present disclosure describes methods and systems for determining source rock potential in a subterranean region of a hydrocarbon reservoir. One method includes: receiving, a terahertz (THz) scanning image from an in-situ THz scanner that is attached to a wellbore at a first subterranean location, wherein the wellbore extends into the subterranean region of the hydrocarbon reservoir; identifying, components of a source rock in the first subterranean location based on the THz scanning image; and determining, the source rock potential at the first subterranean location based on the identified components of the source rock.

13 Claims, 8 Drawing Sheets

(56) References Cited

U.S. PATENT DOCUMENTS

| | | | |
|---|---|---|---|
| 2009/0296086 A1* | 12/2009 | Appel | E21B 49/10 |
| | | | 356/326 |
| 2014/0103904 A1* | 4/2014 | Tan | G01J 1/4257 |
| | | | 324/97 |
| 2015/0046090 A1* | 2/2015 | Chieffo | G01N 33/241 |
| | | | 702/2 |
| 2018/0283171 A1* | 10/2018 | Bhongale | H04J 14/02 |

OTHER PUBLICATIONS

International Search Report and Written Opinion issued in International Application No. PCT/US2018/066201 dated Mar. 15, 2019, 15 pages.

\* cited by examiner

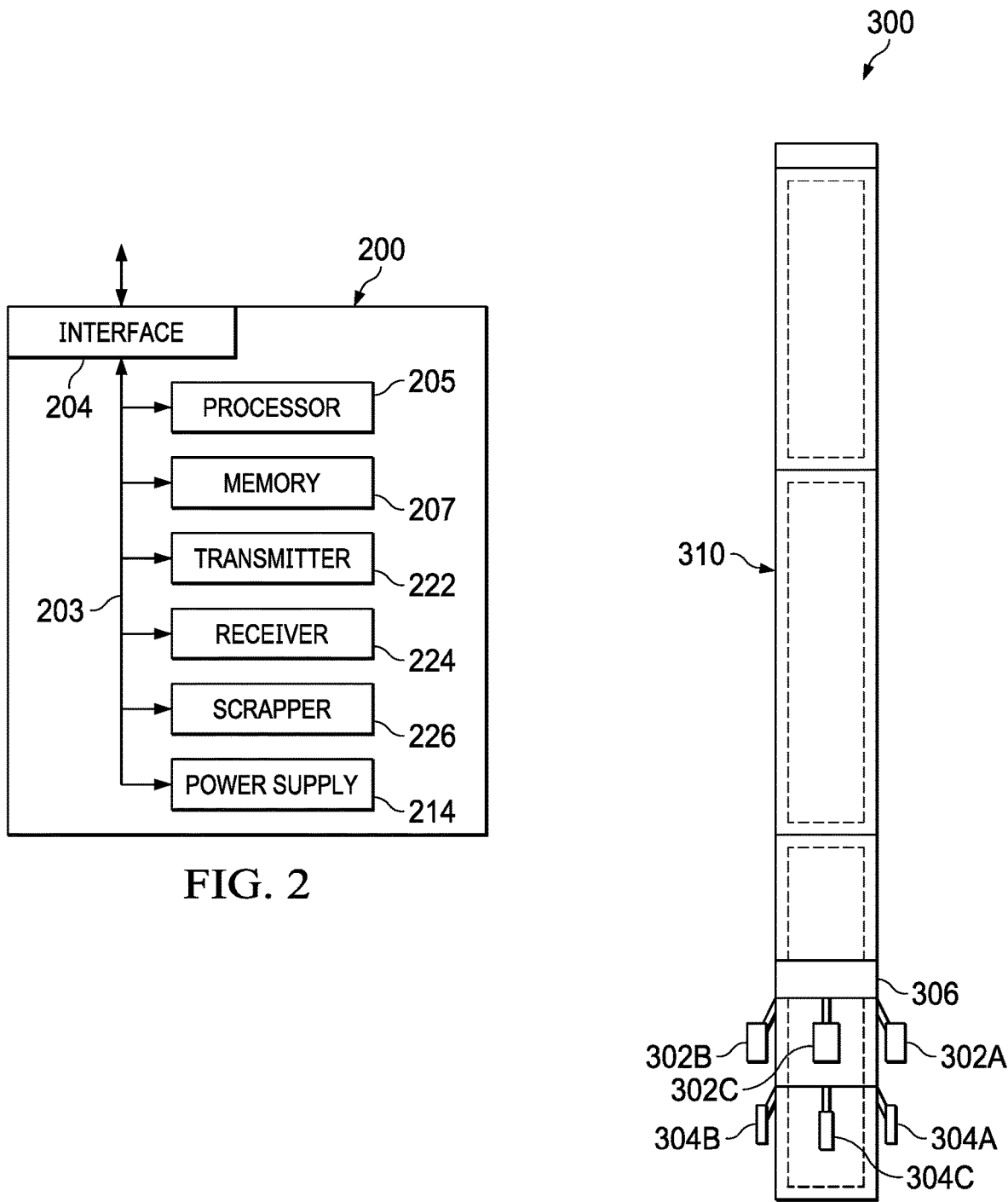

MEASURING SOURCE ROCK POTENTIAL USING TERAHERTZ ANALYSIS

TECHNICAL FIELD

This disclosure relates to measuring source rock potential using Terahertz analysis.

BACKGROUND

In the hydrocarbon production industry, a source rock refers to a rock that is capable of generating or that has generated movable quantities of hydrocarbons. The potential of the source rock refers to the amount of hydrocarbons that may be produced by the source rock. An area may be identified as a reservoir if the area has source rocks that contain organic matter in sufficient quantity to generate and expel hydrocarbons. Measuring source rock potential before and during the exploration and production processes of a reservoir can help to determine the productivity of the reservoir, plan drilling and extraction operations, and maintain the life cycle of the reservoir.

SUMMARY

The present disclosure describes methods and systems for measuring source rock potential using Terahertz analysis. One method includes for determining source rock potential in a subterranean region of a hydrocarbon reservoir, comprising: receiving, a terahertz (THz) scanning image from an in-situ THz scanner that is attached to a wellbore at a first subterranean location, wherein the wellbore extends into the subterranean region of the hydrocarbon reservoir; identifying, components of a source rock in the first subterranean location based on the THz scanning image; and determining, the source rock potential at the first subterranean location based on the identified components of the source rock.

The details of one or more implementations of the subject matter of this disclosure are set forth in the accompanying drawings and the description. Other features, aspects, and advantages of the subject matter will become apparent from the description, the drawings, and the claims.

DESCRIPTION OF DRAWINGS

FIG. 2 is a block diagram of an example in-situ Terahertz (THz) scanner used to measure source rock potential, according to an implementation.

FIG. 3 is a schematic diagram that illustrates an example installation scenario of the in-situ THz scanner, according to an implementation.

Like reference numbers and designations in the various drawings indicate like elements.

DETAILED DESCRIPTION

Figure 1:
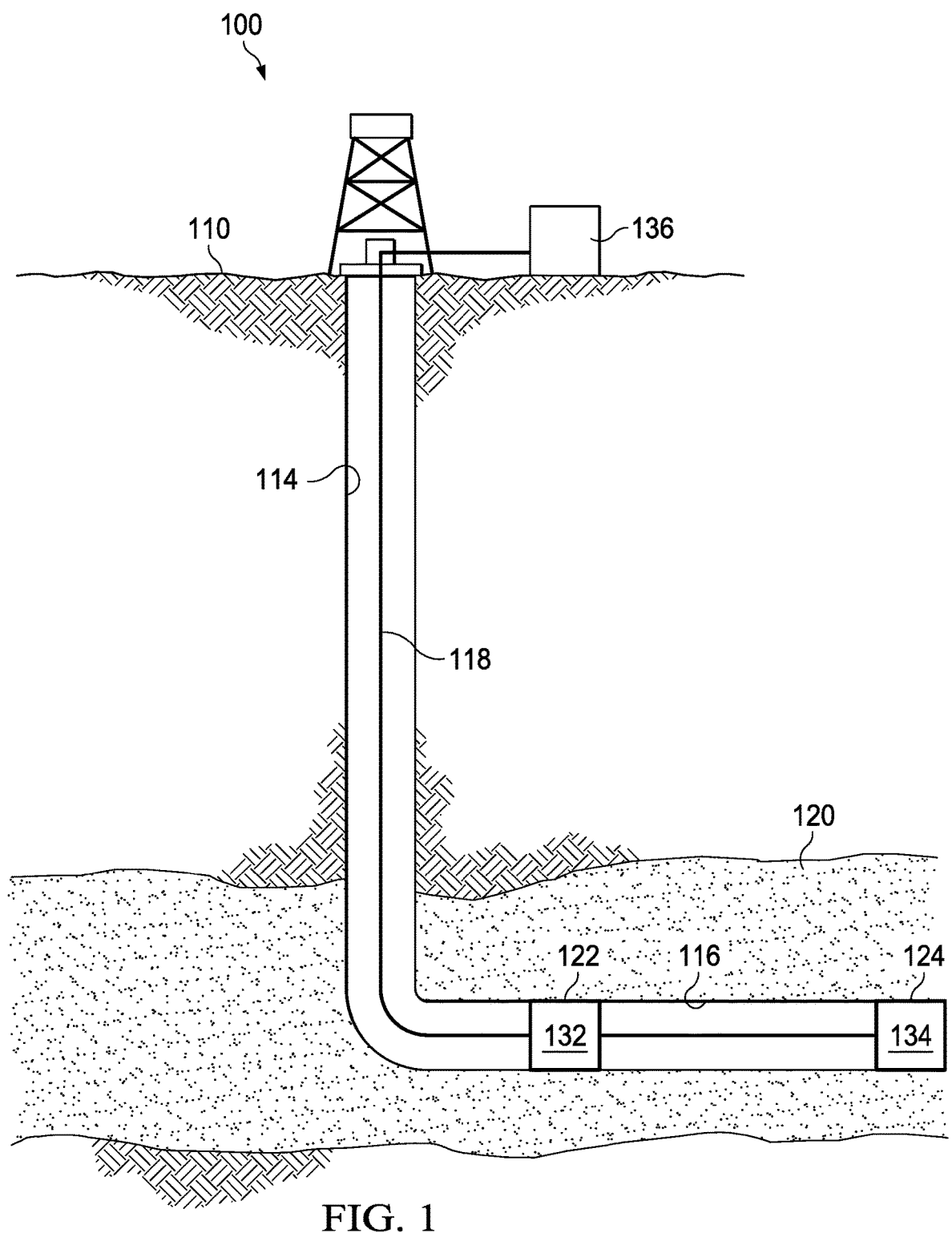
FIG. 1 is a schematic diagram that illustrates an example well system, according to an implementation.

This disclosure generally describes methods and systems for measuring source rock potential using Terahertz (THz) analysis. The source rock potential can be measured by identifying and measuring the molecules in the rock. Molecules have specific electronic, vibration, and rotation levels which can be used to identify them. THz radiations uses electronic magnetic (EM) waves within of frequencies ranging from about 0.3 to about 3 THz. THz radiation can also be referred to as submillimeter radiation, terahertz wave radiation, tremendously high frequency radiation, T-ray radiation, T-wave radiation, T-light radiation, or T-lux radiation.

In some cases, THz radiation can be used to identify and measure molecules in the source rock and determine source rock potential. For example, THz sources can excite rotational levels in molecules such as the ones present in hydrocarbon bearing rocks. Different chemical compounds have different spectral responses to THz radiation. For example, minerals such as Calcite have a higher reflectance than other carbonate minerals at 1 THz. THz radiation can penetrate several millimeters (mms) into the sample and give an image of cores. In some cases, a THz scanning image, can be represented by a plurality of intensity values. Each of the intensity value corresponding a pixel on the THz scanning image. By assigning a color code or a gray scale code to each of the intensity values, the THz scanning image can be rendered, printed, or otherwise outputted. In some implementations, THz waves with different frequencies can be used to scan the sample. Because THz waves with different frequencies can penetrate to different depths of the sample, each scan can generate a 2D image corresponding to a respective depth of the samples. These images can be stacked to provide information on different depths of the sample, sometimes up to 2 mm depending on the frequencies and the nature of the sample. Accordingly, these images can be referred to as 2.5 D images. The measurement results can be analyzed and used as a quantifier for hydrocarbon potential and maturity. In some cases, large areas, for example, several square feet, can be imaged through continuous core scanning.

In some cases, instead of extracting samples from a well and analyzing the samples in a lab, THz device can be miniaturized and placed in a borehole for in-situ measurements. The in-situ THz device can be attached to the outside of a wellbore that extends downward into the subterranean region of a reservoir. The in-situ THz device can also be referred to as the in-situ THz scanner or the in-situ THz scanning device. The in-situ THz device can include one or more low-foot-print THz transmitters and receivers that are constructed using semiconductor components such as silicon-germanium (SiGe), complementary metal-oxide-semiconductor (CMOS), indium phosphide (InP), or gallium arsenide (GaAs). By using these semiconductor components, the in-situ THz device can sustain the high temperature operating environment of a borehole. FIGS. 1-8 and associated descriptions provide additional details of these implementations.

Using the in-situ THz device to perform measurement in a borehole can provide one or more advantages. For example, the measurement results can be processed in real-time to provide assessment of source rock potential to the operating crews in the field, and therefore reduce the turn-around time and improves efficiency. In addition, the in-situ THz device may be easier to transport and install, and therefore reduce the operating expenses incurred by transporting and maintaining bulky THz devices in the field. Moreover, in some cases, a borehole may stretch over a long distance in the subterranean region. In these or other cases, multiple in-situ THz devices can be placed in different locations of the borehole. By receiving and analyzing images of these different in-situ THz devices, source rock potentials at each respective location can be determined. Furthermore, performing THz scanning downhole can enable the scanning of a large image area, and prevent sample damages due to depressurization. Other advantages will be apparent to those of ordinary skill in the art.

FIG. 1 is a schematic diagram that illustrates an example well system 100, according to an implementation. The example well system 100 can use in-situ THz device to generate THz scanning images for rock samples around a wellbore at a subterranean location, as will be described subsequently.

The example well system 100 includes a wellbore 114 extending below the terranean surface 110. The wellbore 114 includes a portion 116 that extends into source rock region 120 in the subterranean area of a reservoir. In some cases, as shown in FIG. 1, the wellbore portion 116 can be positioned horizontally. For example, the wellbore portion 116 can be positioned in parallel to the horizon of the terranean surface 110. In some cases, the wellbore portion 116 can extend to several kilometers.

The well system 100 also includes in-situ THz scanners 132 and 134 that are attached to the wellbore 114. The in-situ THz scanners 132 and 134 can generate THz waves, irradiate THz waves, and generate THz scanning images. The in-situ THz scanners 132 and 134 can transmit the THz scanning images to a master device 136 for analysis. In some implementations, one in-situ THz scanner can be attached to each wellbore. Alternatively or in combination, more than one in-situ THz scanner can be attached to each wellbore. For example, as shown in FIG. 1, the in-situ THz scanners 132 and 134 are attached at different locations (locations 122 and 124, respectively) of the wellbore portion 116. Therefore, each of the in-situ THz scanners 132 and 134 can transmit THz scanning images for rocks at the respective locations. In some cases, the in-situ THz scanners 132 and 134 can transmit an identification of the respective in-situ THz scanner with the THz scanning images generated by the respective in-situ THz scanner. This approach can help the master device 136 to identify THz scanning images generated at different subterranean locations, and determine the source rock potentials at each subterranean location. FIGS. 2-8 and associated descriptions provide additional details of the operations of the in-situ THz scanners.

Figure 5A:
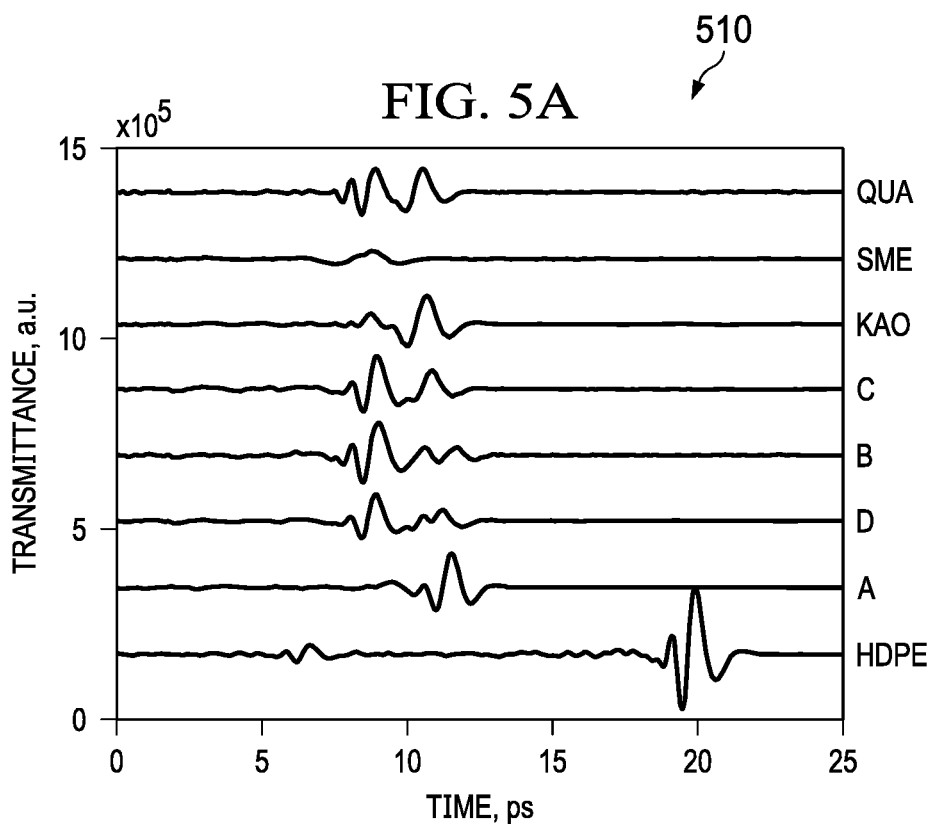
FIG. 5A is a schematic diagram that illustrates example time domain responses for different samples, according to an implementation.

The well system 100 also includes the master device 136. The master device 136 represents a computing device that is configured to receive THz scanning images from the in-situ THz scanners 132 and 134, and analyze the THz scanning images to determine source rock potentials at the subterranean locations 122 and 124, respectively. FIGS. 5A-6 and associated descriptions provide additional details of the operations of the master device 136.

In some cases, the master device 136 and the in-situ THz scanners 132 and 134 can communicate using wireline communication technologies. For example, as shown in FIG. 1, the master device 136 and the in-situ THz scanners 132 and 134 can be connected by a cable 118. The in-situ THz scanners 132 and 134 can use the cable 118 to transmit THz scanning images to the master device 136. The in-situ THz scanners 132 and 134 can also use the cable 118 to receive commands from the master device 136.

In operation, the in-situ THz scanners 132 and 134 generate THz waves, irradiate the THz waves on rocks at the locations 122 and 124, or on rock samples collected from the rocks at the locations 122 and 124, and generate THz scanning images. The in-situ THz scanners 132 and 134 transmit the THz scanning images to the master device 136. The master device 136 analyzes the THz scanning images and determines source rock potentials at the locations 122 and 124. FIGS. 2-8 and associated descriptions provide additional details of these implementations.

FIG. 2 is a block diagram of an example in-situ THz scanner 200 used to measure source rock potential, according to an implementation. At a high level, the in-situ THz scanner 200 includes an interface 204, a processor 205, a memory 207, a system bus 203, a power supply 214, a transmitter 222, a receiver 224, and a scratcher 226. An in-situ THz device may include additional, different, or fewer components as shown in FIG. 2, as appropriate.

In some cases, the example in-situ THz scanner 200, or components of the example in-situ THz scanner 200 can be packaged in a protective case or a pad. The protective case or pad can be constructed using metal, plastic, or any other materials that prevent the scanner 200 or components of the scanner 200 from sustaining damages caused in the subterranean environment. The protective case or pad can also provide good contact with the rock formations around the wellbore and reduce losses in water and air. In some cases, some components, for example, the transmitter 222, the receiver 224, the scratcher 226, or any combinations thereof can be placed outside of the scanner 200. FIG. 3 and associated descriptions provide additional details of these implementations.

Figure 4A:
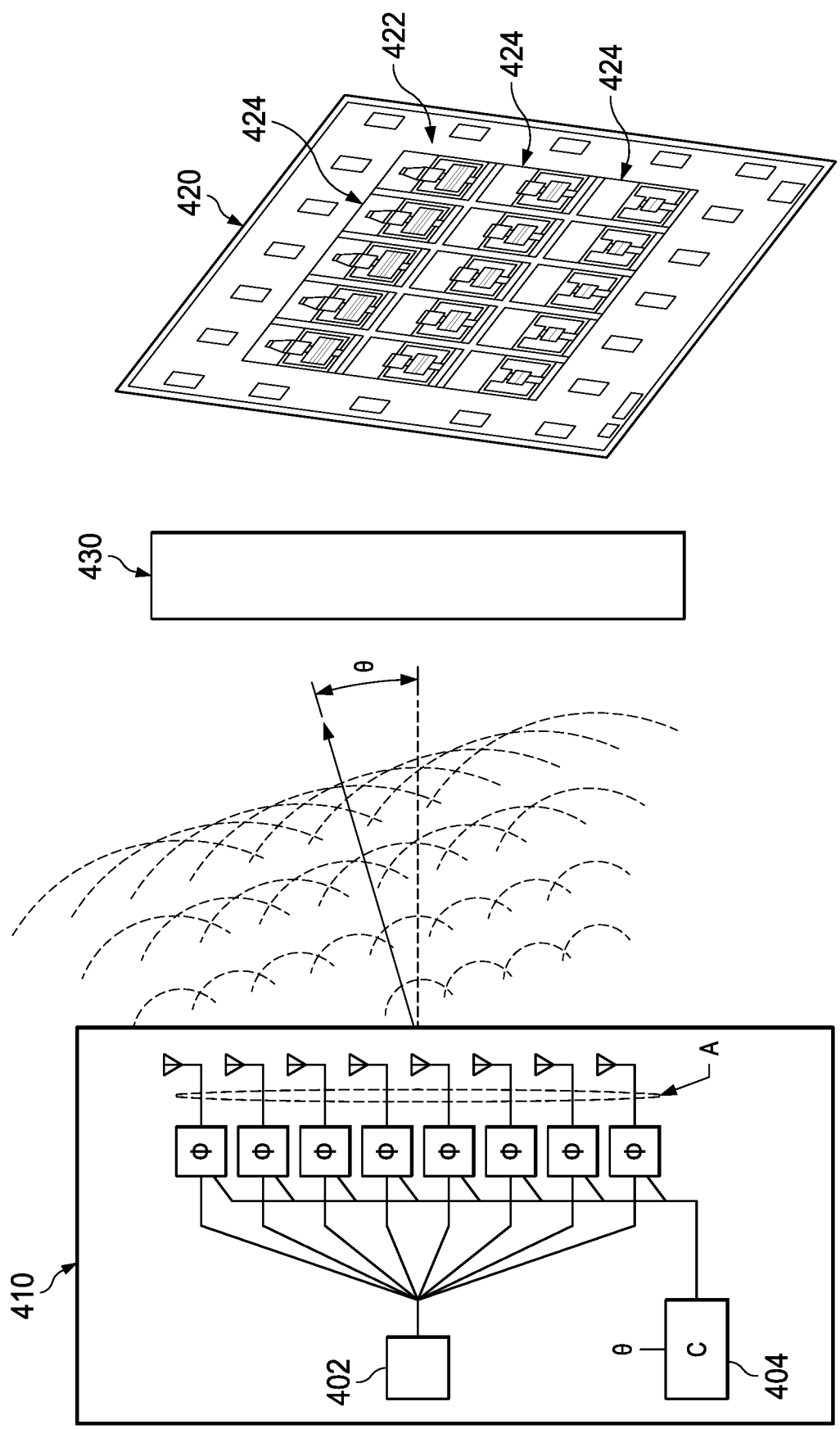
FIG. 4A illustrates an example irradiation operation in a transmission configuration, according to an implementation.
Figure 4B:
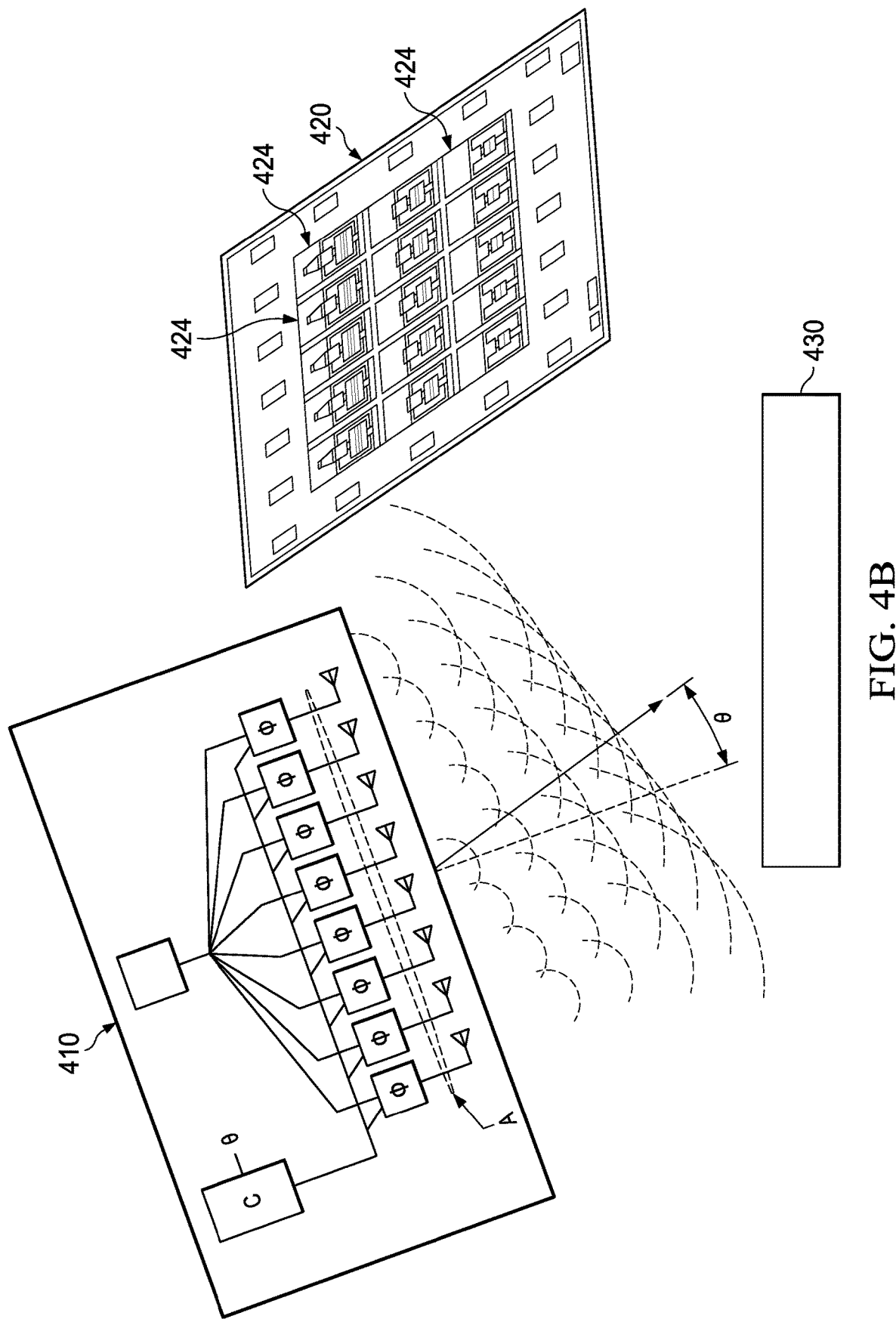
FIG. 4B illustrates an example irradiation operation in a reflection configuration, according to an implementation.

The transmitter 222 generates THz waves to radiate onto the rock samples. In some implementations, the transmitter 222 can be constructed using field effect transistors. FIGS. 4A and 4B and associated descriptions provide additional details of these implementations. The receiver 224 generates images based on the THz waves that are reflected or penetrated through the rock samples. In some implementations, the receiver 224 can be constructed using CMOS. FIGS. 4A and 4B and associated descriptions provide additional details of these implementations.

The scratcher 226 can be configured to scratch the surface of the rock samples. By scratching mud or other borehole fluids from the rock sample, the contamination in the measured signal can be reduced. In some cases, the scratcher 226 can also include components that can be used to take rock samples from the rock formation around the borehole. For example, the scratcher 226 can include an arm that extends outside of the scanner 200 to reach to the rock. The scratcher 226 can also include a claw at the front end of the arm that can scratch the rock surface to make them loose. In some cases, the scratcher 226 can include a collector that collects the loose rock sample, and the transmitter 222 can direct the THz wave to the collected rack sample. In some implementations, instead of taking rock samples for measurement, the transmitter 222 can direct the THz wave to the rock surface around the borehole and the receiver 224 can generate images based on THz wave that is reflected from the rock surface.

Each of the components of the scanner 200 can communicate using the system bus 203. In some implementations, any or all of the components of the scanner 200, hardware or software (or a combination of both hardware and software), may interface with each other or the interface 204 (or a combination of both), over the system bus 203 using standardized or proprietary protocols.

The scanner 200 includes the interface 204. Although illustrated as a single interface 204 in FIG. 2, two or more interfaces 204 may be used according to particular needs, desires, or particular implementations of the scanner 200. The interface 204 is used by the scanner 200 for communicating with other systems that are connected to the scanner 200. For example, the interface 204 may be used to communicate with a master device operating on the surface of the reservoir. The scanner 200 can use the interface 204 to transmit the images generated by the receiver 224 to the master device. The scanner 200 can also use the interface 204 to receive commands from the master device.

Generally, the interface 204 comprises logic encoded in software or hardware (or a combination of software and hardware). More specifically, the interface 204 may comprise software supporting one or more communication protocols associated with communications such that the scanner 200 and is operable to communicate physical signals within and outside of the illustrated scanner 200. The interface 204 can be configured to support wireline or wireless communication protocols that connect the scanner 200 with the master device. For example, the scanner 200 can be connected to the master device using a coaxial cable, an optical cable, a twisted pair, or other wireline communication technologies. Alternatively, the scanner 200 can be connected to the master device using EM waves or other wireless communication technologies.

The scanner 200 includes a processor 205. Although illustrated as a single processor 205 in FIG. 2, two or more processors may be used according to particular needs, desires, or particular implementations of the scanner 200. Generally, the processor 205 executes instructions and manipulates data to perform the operations of the scanner 200 and any algorithms, methods, functions, processes, flows, and procedures, as described in the instant disclosure. For example, the processor 205 can be configured to control the transmitter 222 to generate THz waves and radiate on the rock samples or rock surface around the borehole. The processor 205 can also be configured to form a signal that includes the generated images from the receiver 224 and instruct the interface 204 to transmit the generated images to the master device. The processor 205 can also be configured to control the operations of the scratcher 226.

The scanner 200 also includes a memory 207 that can hold data for the scanner 200. For example, memory 207 can be random access memory (RAM), read only memory (ROM), optical, magnetic, and the like, storing data consistent with this disclosure. In some implementations, memory 207 can be a combination of two or more different types of memory (for example, a combination of RAM and magnetic storage) according to particular needs, desires, or particular implementations of the scanner 200 and the described functionality. Although illustrated as a single memory 207 in FIG. 2, two or more memories 207 (of the same or a combination of types) can be used according to particular needs, desires, or particular implementations of the scanner 200 and the described functionality.

The scanner 200 can also include the power supply 214. The power supply 214 can include a rechargeable or non-rechargeable battery that can be configured to be either user- or non-user-replaceable. In some implementations, the power supply 214 can include power-conversion or management circuits (including recharging, standby, or other power management functionality).

FIG. 3 is a schematic diagram 300 that illustrates an example installation scenario of the in-situ THz scanner, according to an implementation. The diagram 300 includes a wellbore 310 that is located in the subterranean region of a reservoir. The wellbore 310 is surrounded by rocks. The in-situ THz scanner 306 is attached to the wellbore 310. In some cases, as shown in FIG. 3, the in-situ THz scanner 306 is placed outside of the wellbore 310. Alternatively, the THz scanner 306 can be placed inside of the wellbore 310. The THz scanner 306 is connected to transmitters 302a, 302b, and 302c, and receivers 304a, 304b, and 304c. The transmitters 302a-c and receivers 304a-c are attached to the outside of the wellbore 310. In one implementation, the in-situ THz scanner 306 and each of the transmitters and receivers can be placed in a pad that is attached to the outside of the wellbore 310. The pad can be constructed using non-conductive dielectric materials such as Plastics Environmental Council (PEC) plastic, carbon fiber, or high density polyethylene materials. These materials can withstand the high temperature and high pressure in-situ conditions and are transparent to THz waves. Each transmitter corresponds to a respective receiver. For example, the transmitter 302a corresponds to the receiver 304a. In some cases, one set of transmitter and receiver is placed at one location of the wellbore 310. Alternatively, as shown in FIG. 3, multiple sets can be placed at one location of the wellbore 310, while each set is placed at a different side of the wellbore 310.

In operation, the transmitters 302a-c can generate THz waves and irradiate onto the rock surface around the wellbore 310. The receivers 304a-c can receive the reflected wave and generate images based on the reflected wave. In some cases, a scratcher can scratch rock samples from the rock surface and the transmitters 302a-c can direct the THz wave towards the rock samples. The THz scanner 306 can transmit the generated images to the master device on the surface.

FIGS. 4A and 4B illustrate example THz irradiation operations, according to respective implementations. FIG. 4A illustrates an example irradiation operation in a transmission configuration, according to an implementation. FIG. 4A includes a transmitter 410 and a receiver 420 that can be used for in-situ operations described previously.

The transmitter 410 includes a transmitting circuit 402 and a controller 404. The transmitting circuit 402 includes one or more transistors that are configured to generate THz waves. In some implementations, the one or more transistors can be constructed using a wide-bandgap semiconductor (WBGS) such as gallium nitride (GaN). Comparing to conventional semiconductors, WBGS can be configured to operate at high frequency and temperature, and thus are suitable for in-situ operation. In some implementations, the one or more transistors can form radio frequency (RF) components such as a filter, mixer, oscillator, switch, or other components. The transmitter 410 also includes a controller 404. The controller 404 can be configured to control the angle of the THz wave transmitted by the transmitting circuit 402. For example, as illustrated, instead of directing the THz wave in the horizontal direction, the transmitter 410 directs the THz wave at an angle θ away from the horizontal direction. The angle θ can be adjusted by the controller 404. In some implementations, the controller 404 can include one or more phase shifters. In some implementations, the controller 404 can be implemented as part of the transmitting circuit 402.

The receiver 420 includes an electronic circuit that is configured to receive THz waves that are reflected from the rock sample 430 or penetrate through the rock sample 430. In the illustrated example, the receiver 420 includes a printed circuit board (PCB) 422. The PCB 422 includes a sensor array including multiple sensor 424. Each of the sensors 424 represents an electronic circuit unit that detects the intensity of the received THz wave. In some cases, the sensors 424 can be constructed using bipolar CMOS (BiCMOS). As shown in FIG. 4A, the sensors 424 can be organized in a 2D formation. In one example, the 2D formation can include 64 rows×64 columns. In this example, the receiver 420 can generate 64×64 received intensity values based on detected THz waves by each of the sensors 424. As discussed previously, these intensity values form a THz scanning image, where each intensity value represent a pixel on the THz scanning image. The receiver 420 can transmit the THz scanning image to the master device for analysis. In some cases, the receiver 420 can include an on-board memory that stores the THz scanning images and transmit multiple THz scanning images in a batch.

In operation, the transmitter 410 generates the THz wave that is radiated onto the rock sample 430. The sensors 424 on the receiver 420 sense the THz wave that penetrates the rock sample 430 and generates the THz scanning images accordingly.

FIG. 4B illustrates an example irradiation operation in a reflection configuration, according to an implementation. Instead of placing the rock sample 430 between the transmitter 410 and the receiver 420, the rock sample 430 is placed on the same side of the transmitter 410 and the receiver 420. In this scenario, the THz waves generated by the transmitter 410 are reflected from the rock sample 430, and the receiver 420 can generate images based on the reflected THz waves.

Different chemical molecules have different time domain and frequency domain signatures. Therefore, the kerogen content in the source rock can be determined by spectral decomposition of the signals received at the receiver through reflection (as shown in FIG. 4B) or transmission (as shown in FIG. 4A). In some cases, taking images in the reflection configuration may provide a simpler implementation because it may simplify the preparation process of the rock samples.

In some cases, the time domain and frequency domain responses of these different components can be collected and their THz respective transmittance can be measured as a function of vitrinite reflectance. FIG. 5A is a schematic diagram 510 that illustrates example time responses for different samples, according to an implementation. The samples include 4 kerogen samples: A, B, C, and D, each corresponding to a different maturity. The samples also include a quartz (QUA) sample, 2 clay samples: smectite (SME) and kaolinite (KAO), and a Hi-Density Polyethylene (HDPE) sample. In one experiment, these samples were dried in an oven at 60 degrees (C.) for several hours and then placed into a transmission cell. High density polyethylene was used as a material for the cell because this material is transparent in the THZ region. A small indentation of 3 mm in diameter and 1.5 mm depth was used as a place for the samples. After assembling the transmission cell, the samples were kept in a desiccation in order to reduce water contamination prior to THz irradiation. As shown in FIG. 5A, each of these samples shows a distinct time domain signature over time. Here, the x-axis represent time in unit of picosecond (ps), and the y-axis represent the measured transmittance, in units of arbitrary units (a.u.).

Figure 5B:
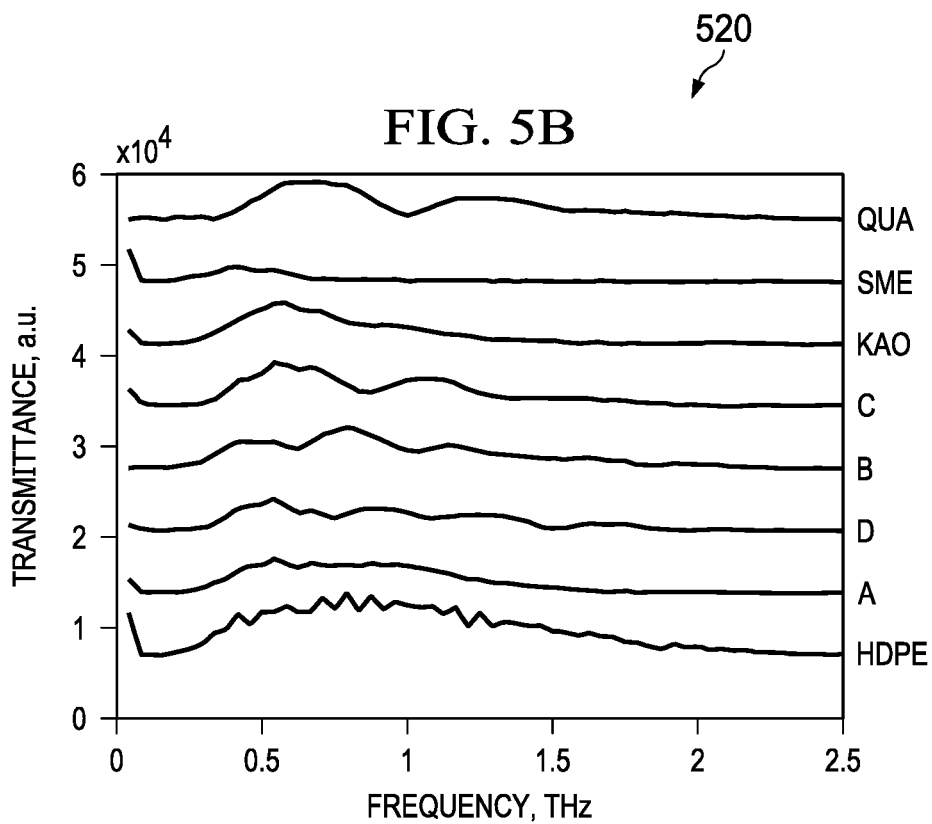
FIG. 5B is a schematic diagram that illustrates example frequency responses for different samples, according to an implementation.
Figure 6:
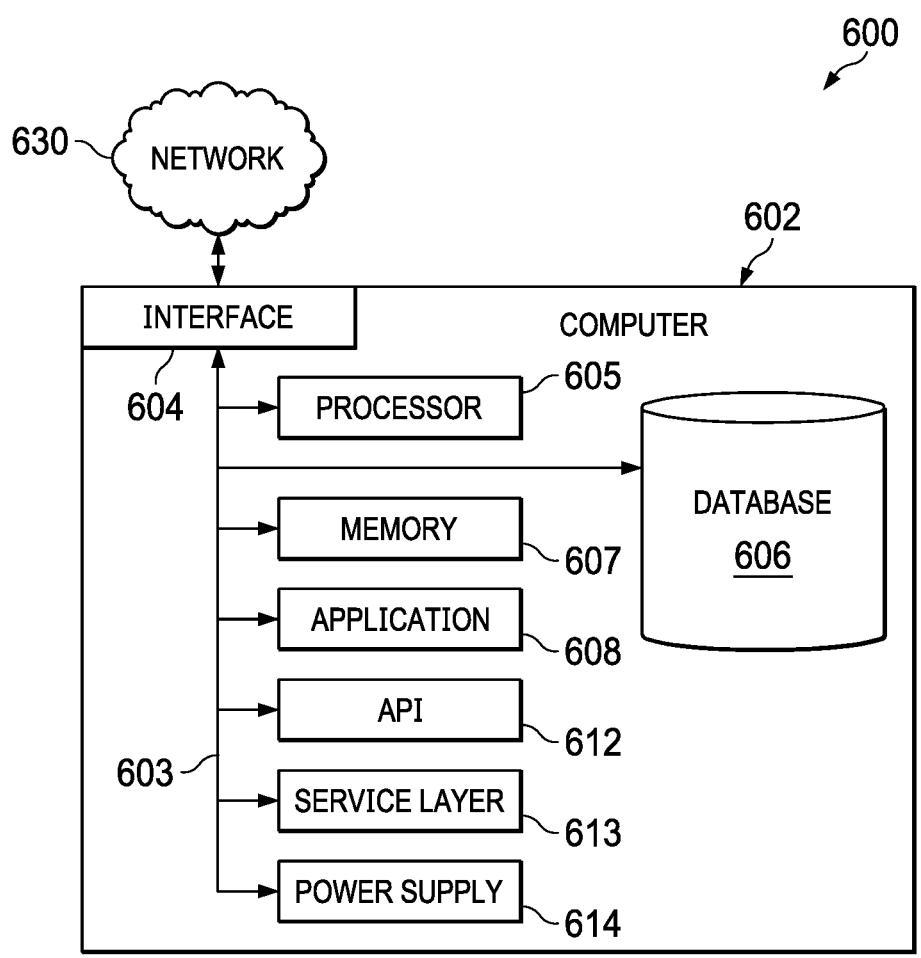
FIG. 6 is a block diagram of an example computer system used to provide computational functionalities associated with described algorithms, methods, functions, processes, flows, and procedures, as described in the instant disclosure, according to an implementation.

FIG. 5B is a schematic diagram 520 that illustrates example frequency domain responses for different samples, according to an implementation. As shown in FIG. 5B, each of these samples shows a distinct frequency domain signature over the range of the THz frequency band. Here, the x-axis represent time in unit of THz, and the y-axis represent the measured transmittance, in units of arbitrary units (a.u.).

These measurements help determine the response of a more complex sample that contains a multitude of components. For example, 2D images for several types of kerogen clays and minerals can be taken in the appropriate THz spectral window to determine the correlation between organic content and maturity. This information can be stored in a database in the master device or can be accessed by the master device. The master device can compare the images taken by the in-situ THz device with the stored images. Based on the comparison, the maturity level of the rock sample radiated by the in-situ THz device can be determined.

In some operations, to obtain the time domain response of a rock sample, different images can be taken by the receiver in the THz scanner periodically over time, for example, at every 5 ps or 10 ps. These images can be stacked over time for analysis. To obtain the frequency domain response, the transmitter in the THz scanner can be configured to transmit THz waves with different frequencies, and the receiver can record the images corresponding to different frequencies accordingly. These images can be stacked over frequency for analysis.

FIG. 6 is a block diagram of an example computer system 600 used to provide computational functionalities associated with described algorithms, methods, functions, processes, flows, and procedures, as described in the instant disclosure, according to an implementation. The computer system 600, or more than one computer system 600, can be used to implement the master device that receives the THz scanning images from the in-situ THz scanner and determines source rock potentials as described previously. The computer system 600, or more than one computer system 600, can also be used to send commands to the in-situ THz scanner to control the operations of the in-situe THz scanner.

The illustrated computer 602 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 602 may comprise a computer that includes an input device, such as a keypad, keyboard, touch screen, or other device that can accept user information, and an output device that conveys information associated with the operation of the computer 602, including digital data, visual, or audio information (or a combination of information), or a graphical user interface (GUI).

The computer 602 can serve in a role as a client, network component, a server, a database or other persistency, or any other component (or a combination of roles) of a computer system for performing the subject matter described in the instant disclosure. The illustrated computer 602 is communicably coupled with a network 630. In some implementations, one or more components of the computer 602 may be configured to operate within environments, including cloud-computing-based, local, global, or other environment (or a combination of environments).

At a high level, the computer 602 is an electronic computing device operable to receive, transmit, process, store, or manage data and information associated with the described subject matter. According to some implementations, the computer 602 may also include, or be communicably coupled with, an application server, e-mail server, web server, caching server, streaming data server, or other server (or a combination of servers).

The computer 602 can receive requests over network 630 from a client application (for example, executing on another computer 602) and respond to the received requests by processing the received requests using an appropriate software application(s). In addition, requests may also be sent to the computer 602 from internal users (for example, from a command console or by other appropriate access methods), external or third-parties, other automated applications, as well as any other appropriate entities, individuals, systems, or computers.

Each of the components of the computer 602 can communicate using a system bus 603. In some implementations, any or all of the components of the computer 602, hardware or software (or a combination of both hardware and software), may interface with each other or the interface 604 (or a combination of both), over the system bus 603 using an application programming interface (API) 612 or a service layer 613 (or a combination of the API 612 and service layer 613). The API 612 may include specifications for routines, data structures, and object classes. The API 612 may be either computer-language independent or dependent and may refer to a complete interface, a single function, or even a set of APIs. The service layer 613 provides software services to the computer 602 or other components (whether or not illustrated) that are communicably coupled to the computer 602. The functionality of the computer 602 may be accessible for all service consumers using this service layer. Software services, such as those provided by the service layer 613, provide reusable, defined functionalities through a defined interface. For example, the interface may be software written in JAVA, C++, or other suitable language providing data in extensible markup language (XML) format or other suitable format. While illustrated as an integrated component of the computer 602, alternative implementations may illustrate the API 612 or the service layer 613 as stand-alone components in relation to other components of the computer 602 or other components (whether or not illustrated) that are communicably coupled to the computer 602. Moreover, any or all parts of the API 612 or the service layer 613 may be implemented as child or sub-modules of another software module, enterprise application, or hardware module without departing from the scope of this disclosure.

The computer 602 includes an interface 604. Although illustrated as a single interface 604 in FIG. 6, two or more interfaces 604 may be used according to particular needs, desires, or particular implementations of the computer 602. The interface 604 is used by the computer 602 for communicating with other systems that are connected to the network 630 (whether illustrated or not) in a distributed environment. Generally, the interface 604 comprises logic encoded in software or hardware (or a combination of software and hardware) and is operable to communicate with the network 630. More specifically, the interface 604 may comprise software supporting one or more communication protocols associated with communications such that the network 630 or interface's hardware is operable to communicate physical signals within and outside of the illustrated computer 602. For example, the interface 604 can be used to receive THz scanning images from the in-situ THz scanner, transmit operating command to the in-situ THz scanner, or a combination thereof.

The computer 602 includes a processor 605. Although illustrated as a single processor 605 in FIG. 6, two or more processors may be used according to particular needs, desires, or particular implementations of the computer 602. Generally, the processor 605 executes instructions and manipulates data to perform the operations of the computer 602 and any algorithms, methods, functions, processes, flows, and procedures as described in the instant disclosure.

The computer 602 also includes a database 606 that can hold data for the computer 602 or other components (or a combination of both) that can be connected to the network 630 (whether illustrated or not). For example, the database 606 can store frequency domain signatures and time domain signatures of known samples that can be used to compare the THz scanning images received from the in-situ THz scanner. The database 606 can be an in-memory, conventional, or other type of database storing data consistent with this disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases (of the same or combination of types) can be used according to particular needs, desires, or particular implementations of the computer 602 and the described functionality. While database 606 is illustrated as an integral component of the computer 602, in alternative implementations, database 606 can be external to the computer 602.

The computer 602 also includes a memory 607 that can hold data for the computer 602 or other components (or a combination of both) that can be connected to the network 630 (whether illustrated or not). For example, memory 607 can be random access memory (RAM), read-only memory (ROM), optical, magnetic, and the like, storing data consistent with this disclosure. In some implementations, memory 607 can be a combination of two or more different types of memory (for example, a combination of RAM and magnetic storage) according to particular needs, desires, or particular implementations of the computer 602 and the described functionality. Although illustrated as a single memory 607 in FIG. 6, two or more memories 607 (of the same or combination of types) can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in this disclosure. For example, application 608 can serve as one or more components, modules, or applications. Further, although illustrated as a single application 608, the application 608 may be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or other power management functionality). In some implementations, the power-supply 614 can include a power plug to allow the computer 602 to be plugged into a wall socket or other power source to, for example, power the computer 602 or recharge a rechargeable battery.

There may be any number of computers 602 associated with, or external to, a computer system containing computer 602, each computer 602 communicating over network 630. Further, the term "client," "user," and other appropriate terminology may be used interchangeably, as appropriate, without departing from the scope of this disclosure. Moreover, this disclosure contemplates that many users may use one computer 602, or that one user may use multiple computers 602.

Figure 7:
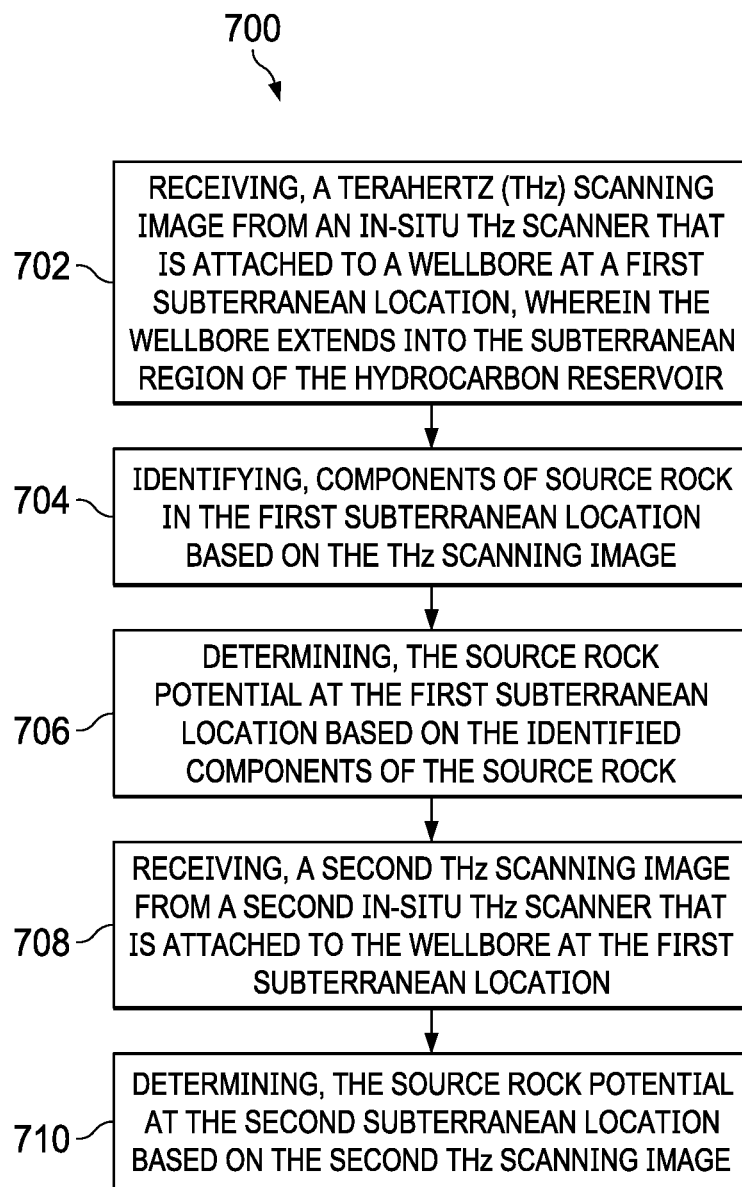
FIG. 7 is a flowchart illustrating an example method for determining source rock potential in a subterranean region of a hydrocarbon reservoir, according to an implementation.

FIG. 7 is a flowchart illustrating an example method 700 for determining source rock potential in a subterranean region of a hydrocarbon reservoir, according to an implementation. The method 700 can be implemented by an electronic device, for example, the master device 136 shown in FIG. 1. The method 700 can also be implemented using additional, fewer, or different entities. Furthermore, the method 700 can also be implemented using additional, fewer, or different operations, which can be performed in the order shown or in a different order. In some instances, an operation or a group of operations can be iterated or repeated, for example, for a specified number of iterations or until a terminating condition is reached.

The example method 700 begins at 702, where a terahertz (THz) scanning image is received from an in-situ THz scanner that is attached to a wellbore at a first subterranean location. The wellbore extends into the subterranean region of the hydrocarbon reservoir. At 704, components of source rock in the first subterranean location are identified based on the THz scanning image. At 706, the source rock potential at the first subterranean location is determined based on the identified components of the source rock. In some cases, at 708, a second THz scanning image is received from a second in-situ THz scanner that is attached to the wellbore at the first subterranean location. At 710, the source rock potential at the second subterranean location is determined based on the second THz scanning image.

Figure 8:
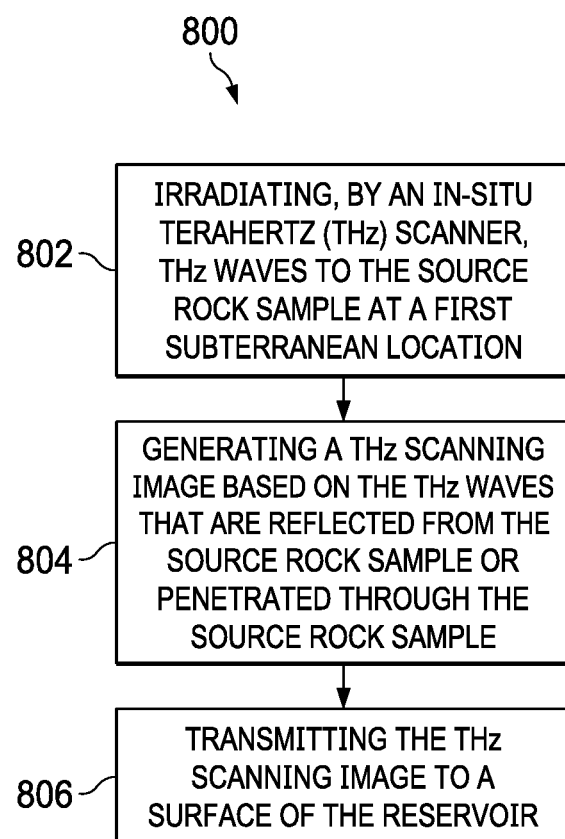
FIG. 8 is a flowchart illustrating an example method for scanning a source rock sample in a subterranean region of a hydrocarbon reservoir, according to an implementation.

FIG. 8 is a flowchart illustrating an example method 800 for scanning a source rock sample in a subterranean region of a hydrocarbon reservoir, according to an implementation. The method 800 can be implemented by an in-situ terahertz (THz) scanner, for example, the in-situ THz scanner 132 or 134 shown in FIG. 1. The method 800 can also be implemented using additional, fewer, or different entities. Furthermore, the method 800 can also be implemented using additional, fewer, or different operations, which can be performed in the order shown or in a different order. In some instances, an operation or a group of operations can be iterated or repeated, for example, for a specified number of iterations or until a terminating condition is reached.

The example method 800 begins at 802, where an in-situ terahertz (THz) scanner irradiates THz waves to the source rock sample at a first subterranean location. At 804, a THz scanning image is generated based on the THz waves that are reflected from the source rock sample or penetrated through the source rock sample. At 806, the THz scanning image is transmitted to a surface of the reservoir.

Described implementations of the subject matter can include one or more features, alone or in combination.

For example, in a first implementation, a method for determining source rock potential in a subterranean region of a hydrocarbon reservoir includes: receiving, a terahertz (THz) scanning image from an in-situ THz scanner that is attached to a wellbore at a first subterranean location, wherein the wellbore extends into the subterranean region of the hydrocarbon reservoir; identifying, components of a source rock in the first subterranean location based on the THz scanning image; and determining, the source rock potential at the first subterranean location based on the identified components of the source rock.

The foregoing and other described implementations can each, optionally, include one or more of the following features:

A first feature, combinable with any of the following features, wherein the in-situ THz scanner comprises a THz transmitter that is attached to the wellbore at the first subterranean location.

A second feature, combinable with any of the previous and following features, wherein the THz transmitter comprises field effect transistors that are constructed using wide-bandgap semiconductor (WBGS).

A third feature, combinable with any of the previous and following features, wherein the in-situ THz scanner comprises a THz receiver that is attached to the wellbore at the first subterranean location.

A fourth feature, combinable with any of the previous and following features, wherein the THz receiver comprises sensors constructed using bipolar complementary metal-oxide-semiconductor (BiCMOS).

A fifth feature, combinable with any of the previous and following features, wherein the THz scanning image is generated by irradiating THz waves at the first subterranean location.

A sixth feature, combinable with any of the previous and following features, the method further comprising receiving, a second THz scanning image from a second in-situ THz scanner that is attached to the wellbore at the first subterranean location; and determining, the source rock potential at the second subterranean location based on the second THz scanning image.

A seventh feature, combinable with any of the previous and following features, wherein both the first subterranean location and the second subterranean location are located on a horizontal portion of the wellbore.

An eighth feature, combinable with any of the previous and following features, wherein the identifying the components of source rock comprises: determining at least one of a time domain response or a frequency domain response of the components based on the THz image; comparing the at least one of the time domain response or the frequency domain response to a time domain signatures or a frequency domain signature of known components; and identifying the components based on the comparison.

A ninth feature, combinable with any of the previous features, the method further comprising: receiving an identification of the in-situ THz scanner that transmits the THz scanning image.

In a second implementation, an in-situ terahertz (THz) scanner includes: a THz transmitter configured to irradiate THz waves to a source rock sample in a first subterranean location of a hydrocarbon reservoir; a THz receiver configured to generate THz scanning images based on the THz waves that are reflected from the source rock sample or penetrated through the source rock sample; and a communication interface configured to transmit the THz scanning image to a surface of the reservoir.

The foregoing and other described implementations can each, optionally, include one or more of the following features:

A first feature, combinable with any of the following features, wherein the THz transmitter comprises field effect transistors that are constructed using wide-bandgap semiconductor (WBGS).

A second feature, combinable with any of the previous and following features, wherein the THz transmitter is attached to a wellbore at the first subterranean location, wherein the wellbore extends into the subterranean region of the hydrocarbon reservoir.

A third feature, combinable with any of the previous and following features, wherein the THz receiver comprises sensors constructed using bipolar complementary metal-oxide-semiconductor (BiCMOS).

A fourth feature, combinable with any of the previous features, wherein the THz receiver is attached to a wellbore at the first subterranean location, wherein the wellbore extends into the subterranean region of the hydrocarbon reservoir.

in a third implementation, a method for scanning a source rock sample in a subterranean region of a hydrocarbon reservoir includes: irradiating, by an in-situ terahertz (THz) scanner, THz waves to the source rock sample at a first subterranean location; generating a THz scanning image based on the THz waves that are reflected from the source rock sample or penetrated through the source rock sample; and transmitting the THz scanning image to a surface of the reservoir.

The foregoing and other described implementations can each, optionally, include one or more of the following features:

A first feature, combinable with any of the following features, wherein the in-situ THz scanner comprises a THz transmitter that is attached to a wellbore at the first subterranean location, and the wellbore extends into the subterranean region of the hydrocarbon reservoir.

A second feature, combinable with any of the previous and following features, wherein the THz transmitter comprises field effect transistors that are constructed using wide-bandgap semiconductor (WBGS).

A third feature, combinable with any of the previous and following features, wherein the in-situ THz scanner comprises a THz receiver that is attached to the wellbore at the first subterranean location.

A fourth feature, combinable with any of the previous features, wherein the THz receiver comprises sensors constructed using bipolar complementary metal-oxide-semiconductor (BiCMOS).

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data may be less than 1 ms, less than 1 sec., or less than 5 secs. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM), or both. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/-R, DVD-RAM, and DVD-ROM disks. The memory may store various objects or data, including caches, classes, frameworks, applications, backup data, jobs, web pages, web page templates, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A method for determining source rock potential in a subterranean region of a hydrocarbon reservoir, comprising:
   receiving, a terahertz (THz) scanning image from an in-situ THz scanner that is attached to a wellbore at a first subterranean location, wherein the wellbore extends into the subterranean region of the hydrocarbon reservoir, wherein the THz scanning image is generated by irradiating THz waves at a rock formation in the first subterranean location and receiving THz waves that are reflected from the rock formation, and the THz scanning image is received with a first identification of the in-situ THz scanner that transmits the THz scanning image;
   receiving, a second THz scanning image from a second in-situ THz scanner that is attached to the wellbore at a second subterranean location, wherein both the first subterranean location and the second subterranean location are located on a horizontal portion of the wellbore, and the second THz scanning image is received with a second identification of the second in-situ THz scanner that transmits the second THz scanning image;
   receiving an identification of the in situ THz scanner that transmits the THz scanning identifying, by using the first and the second identifications, that the THz scanning image is associated with the first subterranean location and the second THz scanning image is associated with the second subterranean location;
   identifying, components of a source rock in the first subterranean location based on the THz scanning image, wherein the identifying the components of a source rock in the rock formation comprises:
      determining a time domain response of the components based on the THz scanning image;
      comparing the time domain response to time domain signatures of a plurality of known components; and
      identifying the components based on the comparing;
   determining, a source rock potential at the first subterranean location based on the identified components of the source rock;
   determining, a source rock potential at the second subterranean location based on the second THz scanning image.

2. The method of claim 1, wherein the in-situ THz scanner comprises a THz transmitter that is attached to the wellbore at the first subterranean location.

3. The method of claim 2, wherein the THz transmitter comprises field effect transistors that are constructed using wide-bandgap semiconductor (WBGS).

4. The method of claim 1, wherein the in-situ THz scanner comprises a THz receiver that is attached to the wellbore at the first subterranean location.

5. The method of claim 4, wherein the THz receiver comprises sensors constructed using bipolar complementary metaloxidesemiconductor (BiCMOS).

6. An in-situ terahertz (THz) scanner, comprising:
   a THz transmitter configured to irradiate THz waves to a rock formation in a first subterranean location of a hydrocarbon reservoir, wherein the THz transmitter is enclosed in a first pad constructed using non-conductive dielectric material;
   a THz receiver configured to generate THz scanning images based on the THz waves that are reflected from the rock formation, wherein the THz receiver is enclosed in a second pad constructed using non-conductive dielectric material;
   a scratcher configured to scratch a surface of the rock formation; and
   a communication interface configured to transmit the THz scanning image with an identification of the in-situ THz scanner to a surface of the hydrocarbon reservoir.

7. The in-situ THz scanner of claim 6, wherein the THz transmitter comprises field effect transistors that are constructed using wide-bandgap semiconductor (WBGS).

8. The in-situ THz scanner of claim 6, wherein the THz transmitter is attached to a wellbore at the first subterranean location, wherein the wellbore extends into a subterranean region of the hydrocarbon reservoir.

9. The in-situ THz scanner of claim 6, wherein the THz receiver comprises sensors constructed using bipolar complementary metal-oxide-semiconductor (BiCMOS).

10. The in-situ THz scanner of claim 6, wherein the THz receiver is attached to a wellbore at the first subterranean location, wherein the wellbore extends into a subterranean region of the hydrocarbon reservoir.

11. A method for scanning a rock formation in a subterranean region of a hydrocarbon reservoir, comprising:
- scratching, by a scratcher of an in-situ terahertz (THz) scanner, a surface of the rock formation at a first subterranean location, wherein the in-situ THz scanner comprises a THz transmitter and a THz receiver, the THz transmitter and the THz receiver are attached to a wellbore, the wellbore extends into the subterranean region of the hydrocarbon reservoir, the THz transmitter is enclosed in a first pad constructed using non-conductive dielectric material, and the THz receiver is enclosed in a second pad constructed using non-conductive dielectric material;
- irradiating, by the THz scanner, THz waves to the rock formation;
- generating a THz scanning image based on the THz waves that are reflected from the rock formation; and
- transmitting the THz scanning image with an identification of the in-situ THz scanner to a surface of the hydrocarbon reservoir.

12. The method of claim 11, wherein the THz transmitter comprises field effect transistors that are constructed using wide-bandgap semiconductor (WBGS).

13. The method of claim 11, wherein the THz receiver comprises sensors constructed using bipolar complementary metal-oxide-semiconductor (BiCMOS).

* * * * *

UNITED STATES PATENT AND TRADEMARK OFFICE
CERTIFICATE OF CORRECTION

PATENT NO. : 10,598,814 B2
APPLICATION NO. : 15/852387
DATED : March 24, 2020
INVENTOR(S) : Sebastian Csutak Page 1 of 1

It is certified that error appears in the above-identified patent and that said Letters Patent is hereby corrected as shown below:

In the Claims

In Column 18, Line 4-5, in Claim 1, before "identifying" please delete "receiving an identification of the in situ THz scanner that transmits the THz scanning".

In Column 18, Line 22, in Claim 1, after "rock;" please insert -- and --.

In Column 18, Line 37, in Claim 5, please replace "metaloxidesemiconductor" with -- metal-oxide-semiconductor --.

Signed and Sealed this
Eighth Day of December, 2020

Andrei Iancu
*Director of the United States Patent and Trademark Office*